United States Patent [19]
Colling

[11] Patent Number: 6,013,834
[45] Date of Patent: Jan. 11, 2000

[54] PRODUCTION OF VINYL ACETATE IN A CATALYTIC REACTOR EQUIPPED WITH FILTER AND DISTRIBUTION BED

[75] Inventor: Philip M. Colling, Corpus Christi, Tex.

[73] Assignee: Celanese International Corporation, Dallas, Tex.

[21] Appl. No.: 09/263,509

[22] Filed: Mar. 4, 1999

[51] Int. Cl.$^7$ .......................... C07C 67/05; C07C 67/00; C07C 69/02
[52] U.S. Cl. .......................... 560/245; 560/241; 560/231
[58] Field of Search .................................. 560/245, 241, 560/231

[56] References Cited

U.S. PATENT DOCUMENTS

| | | | |
|---|---|---|---|
| 5,808,136 | 9/1998 | Tacke et al. | 560/243 |
| 5,831,120 | 11/1998 | Watson et al. | 562/519 |
| 5,859,287 | 1/1999 | Nicolau et al. | 560/241 |

Primary Examiner—Gary Geist
Assistant Examiner—J. Parsa
Attorney, Agent, or Firm—M. Susan Spiering

[57] ABSTRACT

A process for the production of vinyl acetate (VA) by reaction in the vapor phase of ethylene, oxygen and acetic acid as reactants, comprising passing at a temperature sufficient to initiate the reaction, a feed gas comprising said reactants and continuously or intermittently containing liquid acetic acid and/or non-volatile components, through a filter and distribution bed of inert material having throughout its volume substantial intercommunicating open spaces among the solid portions, and thence through a plurality of tubes each containing a bed of catalyst for the reaction, and withdrawing a product gas comprising VA. The filter and distribution bed acts to filter out the liquid acetic acid and/or non-volatile components and distribute more evenly the feed gas into the tubes.

8 Claims, 1 Drawing Sheet

PRODUCTION OF VINYL ACETATE IN A CATALYTIC REACTOR EQUIPPED WITH FILTER AND DISTRIBUTION BED

BACKGROUND OF THE INVENTION

1. Field of the Invention

The invention relates to an improved process of producing vinyl acetate (VA) utilizing a catalytic reactor equipped with a filter and distribution bed.

2. Description of the Related Art

It is known to produce VA by the vapor phase reaction of ethylene, oxygen, and acetic acid using a catalyst, e.g., comprising metallic palladium and gold supported on an inert porous carrier. Such reaction may be carried out in a reactor having the configuration of a tube and shell heat exchanger, i.e., comprising a plurality of tubes, each containing a bed of catalyst and supported between two "sheets" or rigid plates, with the tubes remaining open at each end. The tube and sheet assembly is enclosed in a shell such that the tubesheets separate two end portions of the interior of the shell serving as the inlet and outlet areas for the entering reactants and the exiting products respectively of the VA reaction. The space between the sheets defines the midportion of the interior of the shell through which heat exchange medium, e.g., hot water, surrounding the portions of the tubes containing the catalyst beds, is circulated to absorb much of the heat generated by the exothermic reaction.

A problem associated with the production of VA in a reactor of the type described is that the feed gases in addition to non-condensable recycle gases including ethylene, carbon dioxide, methane, oxygen and others, along with vaporized acetic acid, and heavy ends such as higher esters of acetic acid, may also contain, continuously or intermittently, non-volatile components such as inhibitor residue and polymers, and/or liquid acetic acid. The non-volatile components and/or liquid acetic acid are entrained in the vapor flow from the acetic acid vaporizer and propelled onto the inlet tubesheet of the reactor and into some or all of the tubes. This results in partial plugging of some of the tubes and tneven flow distribution among the reactor tubes, which in turn, results in suboptimum catalyst performance including 'runaway tubes', i.e., reactor tubes which are operating in a mode making mostly carbon dioxide rather than VA. The distribution of the non-volatiles and liquid acetic acid across the tubes may not be uniform so that some of the tubes become more plugged than others. The plugging of the tubes is essentially non-reversible, so that whenever entrainment occurs, the damage that is done remains for the life of the catalyst, unless the VA unit is shut down for reactor entry to vacuum some of the catalyst from the inlet of the tubes and replace it. Thus, the plugging of the tubes seriously reduces the efficiency of the reactor and any expedient which significantly reduces such plugging would be very valuable.

BRIEF SUMMARY OF THE INVENTION

In accordance with this invention, VA is produced by a process of reacting in the vapor phase ethylene, oxygen and acetic acid as reactants, comprising passing at a temperature sufficient to initiate the reaction a feed gas comprising said reactants and which continuously or intermittently contains liquid acetic acid and/or non-volatile components, through a filter and distribution bed of inert material having throughout its volume substantial intercommunicating open spaces among the solid portions, and thence into a plurality of tubes each containing a bed of catalyst for the reaction, and withdrawing a product gas comprising VA. For example, the reactor may have the configuration of a tube and shell heat exchanger containing open-ended tubes secured between two tubesheets as described previously wherein each tube contains a bed of catalyst for the reaction in its midportion between the tubesheets, with a filter and distribution bed of inert material as described, e.g., made up of discrete particles, covering the entire area of the upstream face of the inlet tubesheet. The bed of inert material acts to filter out the liquid acetic acid and/or non-volatiles entrained in the feed gas and to distribute more evenly the feed gas containing such components into the tubes. Thus, the amount of liquid acetic acid and/or non-volatiles entering the catalyst containing tubes is substantially reduced resulting in a lower incidence of the partial plugging of tubes and a significant increase in overall VA productivity.

DETAILED DESCRIPTION OF THE INVENTION

Figure 1:
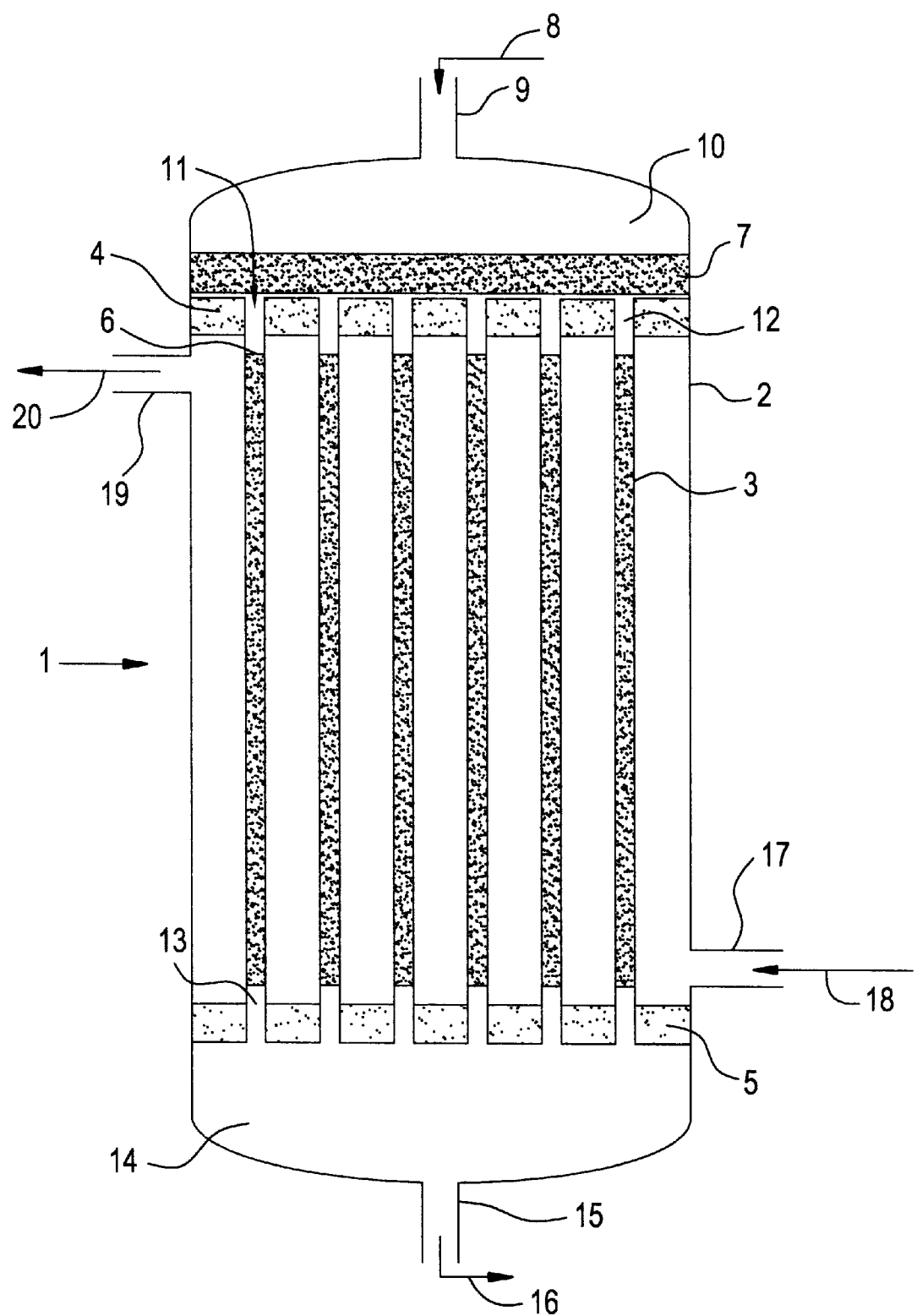
FIG. 1 is a front view of a tube and shell VA reactor showing the presence of catalyst and a filter and distribution bed in accordance with this invention.

An embodiment of this invention involves carrying out the reaction to produce VA, in a reactor having a tube and shell heat exchanger as previously described. The reactor may have any convenient operational position, e.g., vertical wherein the flow of reactants and products is either top to bottom or bottom to top, or horizontal. Preferably, the reactor is vertical wherein the flow of reactants and products is top to bottom. The reactor will have in place the filter bed as described.

The material making up the filter and distribution bed of this invention is inert in the presence of the feed components of the process preheated to the desired inert temperature. Such material is preferably a mass of discrete particles at a size which is effective to distribute more evenly the feed gas into the tubes containing the catalyst bed and filter out a substantial proportion of liquid acetic acid and/or non-volatiles in the feed gas without causing an unduly large pressure drop across the bed. Among the materials which may be used are those which are known in the art to also serve as a satisfactory support or carrier for the catalytically active metals, e.g., palladium and gold, in catalysts for the VA reaction, such as silica, alumina, silica-alumina, titania, zirconia, silicates, aluminosilicates, titanates, spinel, silicon carbide, carbon, and the like. Other materials such as naturally occurring minerals, e.g., granite and basalt, may also be used. The particles making up the bed may have any of various regular or irregular shapes, such as spheres, tablets, cylinders, rings, stars, or other shapes, and may have dimensions such as diameter, length or width, for example, of about 1 to about 10 mm, preferably about 3 to 9 mm. Spheres having a diameter of about 4 to about 8 mm are preferred.

While the inert filter and distribution bed is preferably composed of discrete particles as described, it is also possible to utilize a unitary, i.e., nondiscrete mass of an inert material as long as it meets the criterion of containing intercommunicating open spaces among the solid portions. Such a unitary mass may be made from an inorganic or organic material inert to the reactants and products at the temperature of the VA reaction, e.g., by sintering particles of the material, by forming a rigid or resilient open-celled cellular structure by means well-known in the art, or by forming a non-woven or laminated woven structure of fibers of such material. High temperature-resistant organic material which can be so employed are, for example, organopolysiloxanes and certain completely aromatic polyamides and polyesters.

The depth of the distribution and filter bed is not critical, as long as it accomplishes the desired degree of distribution of feed gas to the inlet ends of the catalyst containing tubes while filtering out enough non-volatiles and/or liquid acetic acid to reduce the occurrence of partial plugging of the tubes. The depth of the bed may be, for example, about 2 to about 36 inches, preferably about 6 to about 12 inches. The greater the depth of the filter bed, the higher the filtering and distribution capacity of the bed, and the higher the pressure drop across the bed. In most cases the pressure drop across the filter bed will be no greater than about 3 psig.

If the VA reactor is in a vertical position with top to bottom flow of feed and product, the bed of inert material can be held in place by gravity during operation, so that no enclosing structure for the material of the bed is necessary to keep such material in position. However, it is often advantageous to provide a system allowing personnel entry into the reactor without crushing the inert bed, for example, a removable open structured stainless steel grating resting on the tubesheet and standing high enough about the tubesheet to protect the filter medium, and constructed in such a way to allow the inert support to pass through the openings. Alternatively, the inert bed could be contained in a frame or cartridge which would be fitted immediately above the top tubesheet.

In the case of a vertical reactor in which the flow of feed and product is bottom to top, or a horizontal reactor wherein the flow is parallel to the ground, the position of the inert bed against the upstream face of the inlet tubesheet obviously would not be maintained by gravity. Thus, in these types of reactor, it is necessary to utilize a support structure, e.g., a frame or cartridge, affixed to the tubesheet, which is completely filled with the inert bed and contains openings smaller than the particles of such bed so that the feed gases can pass through the bed but the particles of the bed are prevented from falling out. Means would also be necessary for replacing the inert bed when spent, e.g., by removing the support structure and replacing it with a structure containing fresh material, or providing the support structure with an adjustable opening through which spent material can be removed and replaced with fresh material.

In carrying out the process of the invention, any catalyst effective in catalyzing the synthesis of VA by reaction of ethylene, oxygen, and acetic acid may be utilized. Preferably the catalyst is one of a type well known in the art in which catalytically active metals comprising palladium and gold are supported on inert porous carrier composed, for example, of any of the materials mentioned previously as suitable for the catalyst support and also for the inert filter and distribution bed of this invention, including the disclosed linear size limitations. However, although not necessary for use in such inert bed, such material when used as a catalyst support preferably has a surface area within the range, for example, of about 10 to about 350, preferably about 100 to about 200 m$^2$/g, an average pore size in the range, for example of about 50 to about 2000 angstroms, and a pore volume in the range, for example, of about 0.1 to 2, preferably about 0.4 to about 1.2 ml/g. The catalyst may contain, for example, about 1 to about 10 grams of elemental palladium and, for example, about 0.5 to about 10 grams of elemental gold per liter of finished catalyst with the amount of gold being from about 10 to about 125 wt. % based on the weight of palladium. Preferably the catalyst also contains an alkali metal acetate, more preferably potassium acetate, in an amount, for example, of about 10 to about 70 grams per liter of finished catalyst.

Referring to FIG. 1, the tube and shell reactor 1 of this invention which employs top to bottom flow is composed of a shell 2 containing tubes 3 secured between rigid inlet tubesheet 4 and outlet tubesheet 5 which are welded or otherwise attached to the inside of shell 2. The exemplified tubesheet is rigid in structure. However, non-rigid means may be employed provided the tubes are held securely in place. Each tube contains a bed of catalyst 6 and resting on the upstream face of tubesheet 4 is a filter and distribution bed 7 of inert material.

In carrying out the process of this invention, a stream of feed gas containing ethylene, oxygen, vaporized acetic acid, heavy ends such as higher esters of acetic acid, non-condensable recycle gases in addition to ethylene and oxygen such as argon, carbon dioxide, methane, and nitrogen gaseous alkali metal acetate and continuously or intermittently, non-volatile components such as inhibitor residue and polymers, and/or liquid acetic acid, is fed through line 8 by means of an inlet nozzle equipped with a distribution or deflection plate (not shown) through inlet 9 of shell 2 into inlet chamber 10. The composition of the feed gas stream can be varied within wide limits, taking in account explosive limits. For example, the molar ratio of ethylene to oxygen can be about 75:25 to about 98:2, the molar ratio of acetic acid to ethylene can be about from 10:1 to about 1:10, preferably about 1:1 to about 1:5, and the content of gaseous alkali metal acetate can be about 1 to about 100 ppm based on the weight of acetic acid employed. The amount of non-volatiles and/or liquid acetic acid present in the feed gas varies with time and may be present in an amount of up to about 5 wt. % or higher based on the total weight of feed gas. The entering feed gas at a temperature, e.g., about 150° C. at which the VA reaction can be initiated, and a pressure which can be reduced, normal or elevated, preferably up to about 20 atmospheres gauge flows through filter and distribution bed 7 of inert material which filters out at least some if not most of the non-volatile components and/or liquid acetic acid, and enters in a more evenly distributed fashion open inlet ends 11 of tubes 3, supported by and passing through the tubesheet 4 and each tube containing a bed of catalyst 6. The top of each bed of catalyst 6 is a short distance below the corresponding opening in tubesheet 4 with the space in tube 3 from the top of catalyst bed 6 to the opening in tubesheet 4 being filled with an inert material 12, which can be the same as that used in filter and distribution bed 7 or any other of the inert materials mentioned previously as suitable for such bed, and which functions as a flame arrester to prevent flashback of a flame into the inlet chamber 10 of the reactor. The feed gas passes through catalyst beds 6 in tubes 3, causing the reactants in the gas to react exothermically to form VA, and the product gas containing VA, unreacted reactants acetic acid, ethylene and oxygen and other non-condensable gases such as by-product $CO_2$, leaves tubes 3 through outlet openings 13 in outlet tubesheet 5, enters outlet chamber 14, leaves the reactor through outlet 15 at a temperature, for example, not exceeding about 220° C., and is transported through line 16 to downstream purification.

It can be seen from the drawing that substantially the complete lengths of tubes 3 containing catalyst beds 6 in their entirety are enclosed in the midportion of shell 2 between tubesheets 4 and 5 such that the exterior of tubes 3 are isolated from the flow of feed and product gases passing through catalyst beds 6. To absorb much of the heat generated by the exothermic reaction and control the temperature of reaction so that it remains within a desired range, e.g. 120–220° C., boiling water as a heat exchange medium, is circulated in the midportion of the reactor enclosing tubes 3 and catalyst beds 6, with the boiling water entering inlet 17 through line 18 and steam and water leaving outlet 19 through line 20.

What is claimed is:

1. A process for the production of vinyl acetate (VA) by reaction in the vapor phase of ethylene, oxygen and acetic acid as reactants, comprising passing at a temperature sufficient to initiate the reaction, a feed gas comprising said reactants, and continuously or intermittently containing liquid acetic acid and/or non-volatile components, through a filter and distribution bed of inert material having throughout its volume substantial intercommunicating open spaces among the solid portions, and into a plurality of tubes each containing a bed of a catalyst for the reaction, and withdrawing a product gas comprising VA, said filter and distribution bed acting to filter out at least some of said liquid acetic acid and/or non-volatile components and distribute more evenly said feed gas into said tubes.

2. The process of claim 1 wherein said reaction is carried out in a reactor having the configuration of a tube and shell heat exchanger containing open-ended tubes secured between two rigid tubesheets wherein each tube contains a bed of catalyst for the reaction in its midportion between the tubesheets, and said filter and distribution bed covers the entire upstream face of the inlet tubesheet.

3. The process of claim 2 where said reactor is in a vertical position and said feed and product gas flow from top to bottom.

4. The process of claim 1 where said inert material is composed of discrete particles.

5. The process of claim 1 where said catalyst comprises a porous support containing catalytically effective amounts of metallic palladium and gold.

6. The process of claim 5 wherein said filter and distribution bed is composed of the same inert discrete particles as the carrier of said catalyst.

7. A distribution filter bed for use in production of VA, comprising a mass of discrete particles at a size which is effective to distribute more evenly a feed gas into reaction tubes containing a catalyst bed, said filter bed to filter out a substantial proportion of non-volatiles in the feed gas without causing an unduly large pressure drop across the bed.

8. The filter bed of claim 7 wherein the discrete particles are selected from the group consisting of silica, alumina, silica-alumina, titania, zirconia, silicates, aluminosilicates, titanates, spinel, silicon carbide, and carbon.

* * * * *